United States Patent
Romans

(10) Patent No.: US 7,015,371 B2
(45) Date of Patent: Mar. 21, 2006

(54) NON-TRAUMATIC MODEL FOR NEUROGENIC PAIN

(76) Inventor: Mary Hannaman Romans, P.O. Box 100996, Fort Worth, TX (US) 76185

( * ) Notice: Subject to any disclaimer, the term of this patent is extended or adjusted under 35 U.S.C. 154(b) by 0 days.

(21) Appl. No.: 09/800,870

(22) Filed: Mar. 7, 2001

(65) Prior Publication Data

US 2003/0139357 A1 Jul. 24, 2003

(51) Int. Cl.
 A01K 67/00 (2006.01)
 A01K 67/033 (2006.01)
 A01K 38/00 (2006.01)
(52) U.S. Cl. .................................. 800/9; 800/8; 514/21
(58) Field of Classification Search ..................... 800/8
 See application file for complete search history.

(56) References Cited

OTHER PUBLICATIONS

Wang, L.X. 2003, Animal and cellular models of chronic pain. Adv. Drug Deliv. Rev. vol. 55, pp. 949-965.*
Petersen, K.L. 2001, Effect of remifentanil on pain and secondary hyperalgesia associated with the heat-capsaicin sinsitization model in healthy volunteers, Anesthesiology, vol. 94, pp. 15-20.*
Lublin, J. 1998, Carpal tunnel syndrome: a review of initial diagnosis and treatment for the OB/GYN, Prim Care Update Ob/Gyns, vol. 5, pp. 280-285.*
Eliav, E., 1999, Neuropathic pain from an experimental neuritis of the rat sciatic nerve, Pain, vol. 83, pp. 169-182.*
Keeton, W and Gould, J., Biological Science, 4th edition, W.W. Norton and Company, paragraph bridging pp. 458-459.*
Lundborg, G. 1982, Median nerve compression in the carpal tunnel-Functional reesponse to experimentally induced controlled pressure, Journal of Hand Surgery, vol. 1, pp. 252-259.*
Wall, 1996, Theriogenology, vol. 45, pp. 57-68.*
Houdebine, 1994, J. Biotech. vol. 34, pp. 269-287.*
Reyna, 1999, ICLAS, Palma de Malloren, May 26-28, p. 226.*
Ford, 1986, Laryngoscope, vol. 96, pp. 1248-1257.*
Allodynia, Stedman's Medical Dictionary, http://216.251.232.159/semdweb/internetsomd/ASP/1526727.asp.*
Hyperalgesia, Stedman's Medical Dictionary, http://216.251.232.159/semdweb/internetsomd/ASP/1526727.asp.*

* cited by examiner

Primary Examiner—Scott D. Priebe
Assistant Examiner—Valarie Bertoglio
(74) Attorney, Agent, or Firm—Howrey LLP

(57) ABSTRACT

Methods for producing nondestructive nerve alterations and/or compressions in animals are provided. The animals provide a model of persistent neurogenic and neuropathic pain in humans. Also provided is a method for screening agents for activity in the treatment of persistent neuropathic pain, as well as methods for use in developing agents for treatment of neuropathic pain. Also provided are methods for detecting and monitoring physiologic changes in persistent pain.

4 Claims, No Drawings

NON-TRAUMATIC MODEL FOR NEUROGENIC PAIN

BACKGROUND OF THE INVENTION

The nervous system routinely sends coded signals that result in sensation. Certain types of lesions to either the central or peripheral nervous system can result in an alteration of sensation resulting in pain. Research into persistent or chronic pain has focused mainly on the spinal cord and brain, with little being done to examine the peripheral nervous system. This is so even though researchers and physicians who treat persistent pain syndromes know that the peripheral nervous system is the origin of much of the pain needing treatment.

Even though the peripheral nervous system is identified as the origin of most persistent pain, such pain usually has no known cause. The lack of knowledge concerning the cause of persistent pain hinders research and development of therapeutics to treat such pain. Many researchers refer to the puzzle of pain when referring to persistent neurogenic pain. The cause of neurogenic pain is only well-defined when there has been a history of direct trauma to the nerve. Most persistent pain, however, develops slowly near an area of soft tissue injury. The basis of the present invention is that persistent pain can develop as a response to often clinically, non-detectable tissue injury, not only as a response to direct trauma. After an injury, there appears to be a functional disturbance of the nerve, leading to demonstration of pain behavior.

Neuropathic pain is defined here as pain attributed to a functional disturbance of a nerve, which can occur as a result of alterations and/or injury to nerves. It can occur by a variety of mechanisms including irritation, injury and compression of the peripheral nerves. The symptoms of neuropathic pain usually include a burning sensation, tingling, or electric-shock-like feelings that may be triggered by even a very light touch. Human persistent pain conditions are organized into two categories: Complex Regional Pain Syndrome I (CRPS I) and Complex Regional Pain Syndrome II (CRPS II). CRPS I refers to pain without obvious nerve injury while CRPS II refers to pain with known nerve injury (Merskey, H. and N. Bogduk. 1994. *Classification of Chronic Pain,* Second Edition, IASP Press). All current animal models involve some type of known nerve injury. Yet, over 90% of persistent pain treated by physicians has no known nerve injury as a cause, although the cause is attributed to being neurogenic in origin. There is a long-standing need for a standard animal model for non-traumatic neurogenic pain, a category into which most patients with persistent neuropathic pain fall.

Any physical change to a nerve can cause physiologic alterations depending on the nerve's receptor organ and the direction of its electric current. Pressure on a nerve is capable of causing nondestructive (non-traumatic) injury to the nerve that can be seen as changes in things such as blood flow of the vasonavorum, accumulation of edema within the nerve, alteration in axonal flow, and a change in the electrical conduction of the nerve. Such changes in pressure on a nerve can result in clinical signs and symptoms of non-destructive nerve injury such as behavioral changes of pain with increased sensitivity to light touch, licking of feet, edema, and increased sensitivity to heat and cold. Other physical examination signs commonly seen that are associated with more traumatic and/or destructive nerve injury would include sensory numbness and/or hyperalgesia to heat or cold, limping, chewing of feet, tremors, spasms, clinical weakness, and/or paralysis. The functional change in a nerve depends on the area and force of pressure applied and the resultant changes in blood flow, lymph circulation, and electrical conductance secondary to the pressure. The consequent alterations in a nerve and their subsequent sensory and behavioral changes may not be immediate, as is seen in a quick high-pressure crush-type injury. In fact, there may be delay of a few days to several weeks before an onset of neuropathic pain after a tissue injury, resulting in a compression of a nerve. Therefore, animal models of nerve pain must consider the physiological changes in tissue during healing that result in a clinical picture of delayed onset persistent neuropathic pain. As a result, models that apply direct trauma or irritants to a nerve are not representative of most human persistent pain. Currently available animal models of neuropathic pain result in acute pain and do not mimic the normal tissue repair physiology which occurs after human injuries. Tissue changes can occur after an injury that lead to altered functioning of a nerve and to ultimate development of pain-related behaviors. No animal model is available that explains the gradual development of pain after an injury.

Current animal models have focused on production of pain through strategies such as irritating, cutting, crushing, ligating, or freezing the nerves in order to model a human peripheral nerve injury. Only rarely would such injuries happen in humans. Examples of such animal models include: use of chemical irritants injected into a limb or paw (Liu-Chen, L. Y. et al. 1991. *Eur. J. Pharmacol.* 15:195–202); transient nerve crush by compressing the nerve with a micro-cuff (Attal, N. et al. 1994. *Pain* 59:301–312); freezing the sciatic nerve using the technique of sciatic cryoneurolysis (Willenbring, S. et al. 1994. *Pain* 58:135–140; Wagner, R. et al. 1995. *Physiol. Behav.* 58:37–41); sciatic nerve partial injury induced by dissecting the nerve into two pieces and only ligating one part (Seltzer, Z. et al. 1990. *Pain* 43:205–218); sciatic nerve partial cut where only a part of the nerve is transected (Dougherty, P. M. et al. 1992. *Brain Res.* 20:109–115); sciatic nerve full cut where the nerve is completely transected (Kingery, W. S. et al. 1999. *Pain* 80:555–566); nerve root ligatures where the lumbar nerve roots are ligated (Kim, S. H. and J. M. Chung. 1992. *Pain* 50:355–363; Choi, Y. et al. 1994. *Pain* 59:369–376); polyethylene cuffs to produce a compression injury (Mosconi, T. and L. Kruger. 1996. *Pain* 64:37–57); use of hemostatic oxidized cellulose that on one side was saturated with an inflammatory stimulus, carrageenan, or complete Freund's adjuvant (Eliav, E. et al. 1999. *Pain* 83:169–182); bee venom injected into rat paw (Chen, H. S. et al. 2000. *Neurosci. Lett.* 284:45–48); scalding of rat paw (Lofgren, O. et al. 1997. *Acta Physiol. Scand.* 161:289–294); photochemically-induced laser lesion of sciatic nerve (Gazelius, B. et al. 1996. *Neuroreport.* 4:2619–2623); use of zymosan on the sciatic nerve (Chacur, M. et al. 2000. *American Pain Society* Poster Presentation); and most recently, spared nerve injury where two or three terminal branches of the sciatic nerve are transected (Decosterd, I. and C. J. Woolf. 2000. *Pain* 87:149–158). All of these animal models rely on production of a destructive nerve injury through direct nerve trauma, irritation, or an immune response. The most popular of these current models for chronic pain is known as the Chronic Constriction Injury (CCI) model where a sciatic nerve injury is induced by tying four chromic gut sutures loosely around the nerve (Bennett, G. J and Y. K. Xie. 1998. *Pain* 33:87–107). However, this model produces animals that have difficulty walking due to the immediate, acute pain and swelling seen in the leg where the procedure is performed. As a result, special attention to animal care is needed for these animals for 3 to 4 days. None of the current models provide animals that are fully ambulatory within minutes of the procedure and require no special care.

The need for a standard animal model for pain without clinical evidence of nerve injury has been recognized and recently preliminary attempts have been made. Reyna et al. (1999. ICLAS, Palma de Malloren '99, May 26–28; 1999) developed an open surgical rat model for CRPS I that involved surgical placement by the tibial nerve of Type II collagen (*American Pain Society Annual Meeting*, November, 2000). This surgical model produced pain responses in the animals characteristic of human persistent neuropathic pain. The responses were delayed in onset by about 14 days. The responses included sensitivity to light touch (mechanical allodynia), and persisted for up to 43 days. In addition, these animals exhibited an analgesic response to morphine sulfate and gabapentin.

Additional models for persistent neuropathic pain are needed, in particular models that require minimal tissue injury.

SUMMARY OF THE INVENTION

The present invention overcomes many of the failures of prior art methods of pain research and pain models. In particular, the present invention provides for the first time a non-surgical, non-traumatic animal model for neurogenic pain where the animals are walking normally within minutes of the procedure with no evidence of immediate, acute pain and require no special care.

An object of the present invention is a method for producing non-traumatic nerve alterations in an animal as a model for persistent neuropathic pain in humans which comprises non-traumatically altering a nerve so that a clinical sign or symptom of a physiologic change in the nerve that is indicative of persistent neurogenic pain is produced in the animal. In one embodiment the non-traumatic alteration of the nerve is gradually produced by injection of a collagen gel substance around the nerve.

Another object of the present invention is detection of physiologic changes near or at the site of neural alteration.

Another object of the present invention is a non-traumatic animal model for persistent neuropathic pain wherein a compression is placed around a nerve non-surgically.

Another object of the present invention is a method for screening treatments for efficacy in the treatment of persistent neuropathic pain which comprises preparing animals for testing by the method of the present invention, testing the animals for the presence of pain behavior or selected physiologic parameters of nerve function before administration of an agent to be tested, administering the agent to be tested, and determining the level of pain behavior or physiologic changes after administration of the agent to be tested, wherein an alteration in the level of pain behavior or the selected physiological parameter as compared to the level before administration of the agent is indicative of efficacy of the treatment tested.

Another object of the present invention is a method for developing treatments for persistent neuropathic pain in humans which comprises screening treatments by the method of the present invention.

Yet another object of the present invention is compositions for the treatment of persistent neuropathic pain that are identified by the method of the present invention.

DETAILED DESCRIPTION OF THE INVENTION

A non-traumatic animal model for persistent neurogenic pain has now been developed in rodents. The present invention is a method for producing a nondestructive alteration near a nerve in an animal that is a model for persistent neurogenic pain in humans, as well as a method for screening agents that could be used in the treatment of persistent neurogenic pain. In the context of the present invention, non-traumatic is defined as a method that does not cause acute pain, an immune reaction, inflammation, or is not due to direct trauma to the nerves by methods that would include but not be limited to direct irritation, cutting, crushing, or binding. Also in the context of the present invention, nondestructive is defined as a condition whereby there are no clinical signs or symptoms (such as paralysis, limping, weakness, erythema, cyanosis, or chewing behavior) of nerve injury and/or no pathological signs of nerve cell death or destruction. Nondestructive nerve injury, however, may be associated with things such as changes in local temperature, hypersensitivity to light touch, heat and/or cold, and possibly tremors or spasms. In the context of the present invention nerve refers to any type of nervous system tissue or cells, in vivo or in vitro, including whole nerve bundles, the spinal cord, the brain, the central nervous system, the autonomic nervous system, isolated nerve cells, neurons, and any type of cellular preparation that includes nervous system cells or tissue, including Schwann cells, glia, and collagen matrix cells. This invention includes all neurogenic alterations to a nerve, including neuropathic. Also in the context of the present invention, physiologic changes around a nerve would include alterations in any of the local hormones, growth factors, cytokines, or gene expression; many of these lead to pain responses or behaviors in an animal, including humans, as well as producing detectable changes in the physiology of the nerve at the site of alteration, where such changes can be detected by present and future imaging methods such as radiography, bioluminescence, or functional MRI.

The focus of the method of the present invention is, therefore, production of a nondestructive, yet maintainable, alteration affecting a nerve. This may be accomplished by a variety of methods that would include but not be limited to placement of a biocompatible substance in proximity to the nerve, either directly or indirectly, surgical as well non-surgical placement of the biocompatible substance, as well as use of transcutaneous, percutaneous or external forces to apply pressure on the nerve. In most instances, in order to produce a nondestructive, physiological alteration to a nerve, it is necessary to have the presence or creation of a biocompatible substance, wherein a biocompatible substance is one that does not immediately produce any irritation or inflammatory response or any physiological response that would lead to immunological reaction to the substance in the body, and would include evidence of any acute pain. Such biocompatible substances would include but not be limited to collagen, fibrin, fibronectin, cellular extracts with other cells such as fibroblasts, the addition of stimulative cytokines, growth factors and/or hormones, elastin, autogenic extracts of stimulative cells, or any other biological or inert substance or substances that when administered either alone or in combination would directly or indirectly stimulate collagen production. Of particular interest are biocompatible substances in a viscous or colloidal form, herein referred to as gels, and those that have an elastic body that can produce an elastic deformation of the nerve cells, wherein an elastic deformation is defined as a change in the shape of the nerves. The biocompatible substance chosen for use in the present invention is capable of generating a mechanical force on the nerve in a nondestructive manner, wherein a nondestructive manner is defined as a manner wherein no discernable neurological deficit could be identified clinically in the animal. Although in the present invention the biocompatible substance is used in a whole animal model in rodents for persistent neuropathic pain, the same method of inducing a neural alteration with a biocompatible substance can be applied to other nerves such as various unicellular neurocytes, nerve cells or nerve nets of coelenterata, nerve cells including the giant axons of annelida, squid, and mollusca phylum among the invertebrates, as well as the neurons or related nerves of the peripheral, autonomic and central nervous system of vertebrates such as fish, amphibians, reptiles, birds, and mammals other than rodents, including humans. This invention also includes application of the model of the present invention to all embryonics, clones, single nucleotide polymorphisms and transgenics in the cells and organisms mentioned above.

Since a wide variety of biocompatible substances may be used in the present invention, ones with a large variety of molecular structures, densities, and fluidities, the substance chosen for use may vary. The factors to consider when choosing a biocompatible substance for use in the present invention include the ability of the substance to not induce an immune reactions or immediate inflammatory reaction within its immediate environment, as well as the nature of the substance which allows for direct or indirect production of a physiological nondestructive alteration or pressure on a nerve. The substance may be inert, biodegradable, or produce physiological alterations in the nerve or its environment. Thus, the preferred substance must be both biocompatible and capable of producing or inducing nondestructive alterations and/or pressure on the nerve. Many polymers currently used in surgical and cosmetic procedures in humans and animals are biocompatible with rare immunogenic reactions and can be used in the creation of the neural alteration of the present invention. These substances would include but not be limited to any type of suture material, any hemostatic agent, or any material used in general, cardiothoracic, or plastic surgery of animals. Examples would include but not be limited to polyglycolic acid, colloids or suspensions with racemic forms of lactic acid, and emulsions with an oleaginous medium. Sclerosing agents such as formaldehyde and propylene glycol act by changing the nature of tissue in vivo by processes such as protein alteration or dehydration. These and similar processes can stimulate the tissue repair process with the production of collagen resulting. Included in the present invention are any agents which non-immunogenically alter or harden tissues in vivo, ultimately resulting in fibrosis.

The biocompatible substance used in the present invention is usually placed so as to surround or contact the chosen nerves. Particularly useful thus are substances which provide for a circumferential elastic force to be placed on the nerve. This substance does not have to surround or be in a circular position to produce a circumferential force. Instead, the substance could produce a force that is irregular in shape or even triangular. The substance may directly or indirectly produce a compressive force or induce a physiological reaction to create a neural alteration.

Methods for delivery of the biocompatible substance to the site of production of the nondestructive compression injury in the present invention are non-traumatic and minimally invasive methods. In the context of the present invention non-surgical is defined as a method that does not rely on an open surgical incision of the skin or any other tissue for open, visualized placement of a biocompatible substance. The biocompatible substance is placed percutaneously by a skilled operator or by using microscopic techniques that could include fiberoptics and endoscopy. In the context of the present invention, a skilled operator is a person or machine performing this method on a living organism with any device, tool or method that places the biocompatible substance by the identified nerve. These would include but not be limited to a needle and syringe. In a preferred embodiment the placement device is a hypodermic needle with a 30 to 45 degree angle constructed with the needle bevel facing upwards. One of skill would choose the size and angle of the needle used based on the animal to be used in the model for placement of the gel around the nerve. In the present invention needles of 23 gauge have been used.

The biocompatible substance used in the present invention can be any molecular/polymer complex capable of inducing physiologic alterations or pressure to a nerve through either direct or indirect reactions. The substances can include those that produce either immediate or delayed reactions. Therefore, the present invention could employ elastic biomaterials or solids or liquids which change their consistency at body temperature to provide an alteration by the nerve. Examples of such other substances would include but not be limited to inflatable or deformable membranes, a gas reaction substance, a magnetic or electromagnetic gel, mutated or genetic variants or transgenic organisms created to induce the desired alteration, expandable or collapsible mesh structures, electric, or magnetic methods with or without biochemical mechanisms or enzymes, and any mechanical device or method which creates an increase in neural physiologic pressure, temporarily or permanently, to include methods such as nanotechnology and bioengineering. Also useful would be substances that directly or indirectly increase the production of collagen or collagen-related changes in tissue, substances that would include fibrin, antibodies, antigens, fibroblasts, stimulating hormones, growth factors, and cytokines, among others.

After the alteration or compression of the nerve has been produced, either by the method of the present invention or by nature (i.e., a naturally-induced nondestructive nerve alteration), the change in the local physiology of the nerve may be detected non-invasively. Neural alterations can result in changes or dysfunction related to processes that would include but not be limited to neural regeneration, neural edema, neural inflammation, mechanical pressure, blood flow, and electrical conductivity. All of these alterations can produce changes that can be detected or imaged by present and future methods. Therefore, also contemplated by the present invention are methods for developing detection or monitoring instruments, devices, or techniques for detection of non-observable physiologic changes consequent to the development of neural alterations, such as temperature changes, alterations in electrical conductivity, or changes in substances produced by the nervous system or other bodily tissues or systems. These physiological changes may occur at the local area of neural alteration or occur elsewhere in the organism's body.

The method of the present invention is a method for producing a nondestructive nerve alteration or compression in vivo in an animal that is a non-traumatic model for persistent neuropathic pain in humans. The model involves altering the local physiology or compressing a nerve in an animal so that a clinical sign or physiologic change is detected, wherein that sign is indicative of persistent neurogenic pain. In one embodiment the method for producing the nondestructive nerve alteration is due to injection of a collagen gel substance around a nerve. The clinical sign of neurogenic pain can be any form of spontaneous or elicited pain behavior, including mechanical allodynia (i.e., hypersensitivity to light touch). Therefore, the present invention is a non-traumatic animal model for persistent neurogenic pain wherein a biocompatible substance is placed near a nerve to induce an alteration or compression. The present invention is also a method of detecting and monitoring persistent neurogenic pain in vivo wherein the physiological changes in the cell or organism that are indicative of nerve compression are detected. The present invention includes methods for screening treatments for efficacy in the treatment of persistent neurogenic pain comprising employing the animal model of the present invention and testing those animals for the presence of clinical or physiological signs of nondestructive nerve compression or alteration both before and after administration of an agent to be tested for therapeutic activity or efficacy. As a result, the present invention is also a method for developing treatments for persistent neurogenic pain in humans wherein the treatments are screened or developed by the method of the present invention. Compositions for treatment of persistent neuropathic pain in humans are also contemplated by the present invention, as are compositions identified by the method of the present invention.

Thus, an animal model for persistent neuropathic pain in humans was developed that is both non-surgical, non-traumatic and can produce clinically, nondestructive nerve alterations or compressions. The animal model is based on the detection of pain behavior in rodents. Retired male breeder mice (5 AKR/J and 5 C57BL/6J) were housed singly. Baseline von Frey testing for pain behavior, in this case mechanical allodynia, was performed on three different days over a one week period and the results were averaged. In the method of von Frey testing for sensitivity to light touch, the plantar hind paw on the left leg was used for testing. At regular intervals, the response of the paw to light touch in terms of paw withdrawal was tested. Light touch was provided with a camel hair brush as well as two different von Frey fibers (4.13 and 4.73). All light touch stimuli (1 brush and 2 von Frey fibers) were touched to the left paw ten times each and the number of paw withdrawals was recorded. These stimulation tools are standard tools used in determining pain behavior to the normally non-painful stimulus of a light touch (mechanical allodynia).

Type II collagen was prepared for use in the method of production of a nerve compression The Type II collagen source was dry gelatin that was prepared using sterile techniques. The dry collagen was measured to 2.5 cc and mixed with 7.5 cc of sterile normal saline. The mixture was heated for 30 seconds in a microwave on 80% power, The mixture was kept soft in warm water (approximately 100 to 110 degrees). The consistency of the resulting collagen was such that it was able pass through a 23 gauge needle. Humidity and other factors such as temperature can affect the consistency of the substance. One cc syringes were used for injection of 0.2 to 0.25 cc of collagen. For the injection, 23 gauge one inch standard luer lock hypodermic needles were used. The needles were very slightly dulled with a metal file at the tip and edges using sterile technique. The needles were angled at the midpoint with a bevel tip up. The angle was between 30 and 45 degrees, but any angle that allows for easy placement of the injected substance could be used. The needles were then attached to the collagen-filled one cc syringes. The syringes were kept in a warm water bath (100 to 110 degrees) to maintain proper gel consistency.

Mice were lightly anesthetized with 1.5 to 2% isoflurane. The mice were stabilized and aligned such that the left posterior leg was in view. The external anatomic landmarks of the posterior popliteal were identified. The internal anatomy of this area including the posterior tibial nerve with its artery was mentally visualized with kinesthetic techniques. Kinesthetic techniques are techniques that use the kinesthetic sense or the sense by which movement, weight and position are commonly perceived. It also refers to the integrated use of multiple senses such as touch, proprioception, vision, and hearing. After location of the site for placement of the gel, the needle and syringe were then removed from the warm water bath. The distal portion of the needle was held loosely parallel to the tibia. The needle was allowed to gently penetrate through the dermis by pulling the skin taut over the popliteal fossa. With careful avoidance of tissue resistance, the needle tip, bevel up, was gently slipped beneath the fascial edge of the soleus muscle by the tibial nerve and artery into the deep posterior fascial compartment of the posterior tibial neurovascular tunnel, which is the neurovascular tunnel for the posterior tibial nerve and its proximal branches. When the tip of the needle was at the mid soleus muscle belly, the collagen mixture was slowly injected into the posterior tibial tunnel. The needle was removed and the animals allowed to recover from the anesthetic. All animals were normally moving freely within 20 minutes of anesthesia withdrawal.

Two days after placement of the collagen gel around the nerve, von Frey testing was again performed. Von Frey testing continued for 49 days. On day 49 post placement of the collagen, analgesic testing was initiated using morphine sulfate (1 and 5 mg/kg) and gabapentin (25 and 40 mg/kg). The results of the testing for mechanical allodynia are presented below in Table 1.

TABLE 1

Results of von Frey Testing in Mice with Neural Compression (n = 10)

| Day of Testing/Conditions | Average # Paw Withdrawals |
|---|---|
| Baseline testing | 3.59 |
| Post procedure day 2 | 2.78 |
| Post procedure day 7 | 2.37 |
| Post procedure day 9 | 4.29 |
| Post procedure day 14 | 6.22 |
| Post procedure day 23 | 5.67 |
| Post procedure day 30 | 8.08 |
| Post procedure day 42 | 8.75 |
| Post procedure day 49 | 8.71 |
| Plus morphine (1 mg/kg) | 8.71 |
| Post procedure day 51 | 8.88 |
| Plus morphine (5 mg/kg) | 6.66 |
| Post procedure day 58 | 9.14 |
| Plus gabapentin (25 mg/kg) | 6.86 |
| Post procedure day 65 | 9.19 |
| Plus gabapentin (40 mg/kg) | 5.81 |
| Post procedure day 73 | 9.24 |
| Post procedure day 79 | 9.48 |
| Post procedure day 86 | 8.67 |
| Post procedure day 107 | 8.33 |

The higher numbers correlate with an increase in the pain behavior of mechanical allodynia. All mice demonstrated mechanical allodynia within two to three weeks of placement of the collagen. Within 14 days, the differences in responses were statistically significant from baseline levels. The response continued for the entire period of the experiment or 107 days. Analgesic responses were shown when doses of morphine were at least 5 mg/kg and doses of gabapentin were either 25 or 40 mg/kg.

These data demonstrated that the method of the present invention provided for an animal model that was non-surgical and produced a known pain behavior that could be reliably produced. The abnormal response to light touch is known as mechanical allodynia and is currently the most sought-after pain behavior in animal models of neuropathic and neurogenic pain.

The present invention is also a method for screening for substances that can be used to treat persistent neuropathic pain in animals, including humans. The data described above for the known analgesic compounds, morphine and gabapentin, demonstrate the use of the present invention, a percutaneous animal model of nondestructive nerve alteration and/or compression. Substances under development for testing of analgesic activity, or any process or device useful for treatment of neuropathic pain, would be screened or developed through use of the animal model of the present invention. Behavioral or physiologic responses of the animals at baseline, before placement of the biocompatible substance two to four weeks after placement, and then after administration of doses of the substance to be tested for analgesic activity would be determined. In the context of the present invention, behavioral and physiologic responses would include but not be limited to: 1) any observable behavior change such as reactions to heat, cold vibration, pinprick, light, or light touch by any method; and 2) any non-observable physiologic reactions at the cellular (i.e., changes in gene expression, growth factors, cytokines, enzymes, regeneration, or other cellular products, ion channels, adhesion moletics apoptosis, proteins levels, metabolism, pressure, receptor activity or numbers, form, and/or anatomy) and molecular (i.e., changes in function, action, mechanics, products, or ligands) level. These behavioral and/or physiological responses may occur as a result of changes in the nervous, circulatory, endocrine and/or lymph system of an animal. Differences in responses after administration of the test substance as compared to responses after placement of the compression would indicate that the substance being tested is a candidate for treatment of humans. One of skill would understand that the method of the present invention for screening new substances is one part of the drug development process for human therapeutics and would proceed with further development based on the results of the animal model testing of the present invention. Therefore, the present invention is also a method for development of drugs or substances or devices or methods for treatment of neurogenic pain. The non-traumatic methods of the invention can lead to new cell and/or gene based drug screening techniques, such as high throughput drug screening assays, providing a powerful new approach to drug development. Thus, certain preferred results of the method will be treatments, including drug and screening techniques identified by the present invention, related to the research and development of pain diagnosis and treatment.

Therefore, one of skill would use this method of screening to develop treatments for nondestructive nerve injury. Techniques or treatments that are capable of relaxing or releasing a nerve compression, or changing the induced neural alterations, would be identified with the use of the animals produced in the present invention. Therefore, the use of the method of the present invention would include screening for any substance or technique that alters the physiology of the neuron at the site of compression to reduce symptoms related to nondestructive nerve injury. Treatments that could be tested using the method of the present invention would include all optic, facial, oral, intraperitoneal, fascial, intramuscular, intravenous, transcutaneous, subcutaneous, cutaneous, nasal, and/or rectal and vaginal or genital treatments.

Since the method of the present invention is a nondestructive, non-traumatic method, also contemplated by the present invention would be cellular or physiological simulation programs that model neural networks that govern cell behavior. Examples of such programs in early development would be E-CELL and VIRTUAL CELLS. Therefore, the present invention would include any software program or cell screening assay which simulates any of the neural alterations demonstrated in this invention. Since changes near a cell can affect individual cell and cell group biochemical processes, any programs which simulate the reaction of a nerve or its environment to neural changes found in this model are included in the present invention.

Based on the knowledge that non-traumatic alterations and compression of a nerve can result in no obvious signs of nerve injury other than persistent pain, a method of detection of naturally-occurring neural alterations or compression was sought and discovered and then shown to be effective in humans. Evidence of neural compression in humans has been based on a clinical examination involving palpation for tenderness and/or dysesthesias (Tinel's signs). The examination can also be done based on changes in electrophysiological parameters or clinical sensory testing, or biomechanical provocative testing. MRI imaging has also been used to visualize neuroanatomical structural changes. However, the use of MRI techniques has been limited to changes in large nerve bundles and the central nervous system. The present invention provides a method for localizing altered neural physiology. The tool used to detect the changes is a receiver device that amplifies electrical signals from neural tissue. In human patients with complaints of neurogenic pain, without a history or evidence of direct trauma or nerve transection, the device has detected distinctive electrical signal changes at or near the sites of neural alterations or compressions.

The following non-limiting examples are provided to further illustrate the present invention.

EXAMPLES

Example 1

A Rat Model of Persistent Neuropathic Pain

Male rats (350 to 400 g) were housed singly. Over ten days four periods of baseline behavioral testing to mechanical light touch, pinprick, heat and cold applied to the plantar surface of the left hind paw were performed for control data. All testing was done in an open cage without restraints. Light touch was tested with five von Frey fibers (3.61, 4.31, 4.74, 4.93 and 5.18) with ten stimulations of each fiber, 2 to 4 seconds apart in ascending order of pressure in each testing period. Pinprick was tested with a sharp, non-penetrating metal point adhered to a postage scale (point up) and gently pressed against each paw with a weight reading taken at time of paw withdrawal. This test was performed 6 times in each testing period. Heat and cold responses were tested with a large, peltier type floor thermode. The temperature was gradually raised (32 to 50 C) to test heat responses and cold was tested by gradually lowering the temperature (32 to 5 C). The temperature was returned to 32 C on ipsilateral hind paw withdrawal. The heat and cold stimulations were done 6 times each in separate sessions. Ipsilateral hind paw withdrawal was considered the positive endpoint in testing of all stimulation types noted.

After establishing baseline responses in each animal, the material for placement near the nerve was prepared. The preferred substance was sterile, purified Type I collagen (5 mg/ml) neutralized and mixed to a 5% sterile normal saline solution (pH 7.4). This mixture was kept under refrigeration and used while still cold as it can solidify at warmer temperatures. Humidity, pH, and temperature in the room can affect the consistency of the collagen. The consistency needs to be fluid enough for passage through a 23 gauge needle. A 0.2 cc sample of collagen was drawn into a cold 1 cc syringe with a 23 gauge one inch hypodermic needle and then refrigerated.

The animals to be injected were lightly anesthetized and shaved at the left medial thigh. An open, transcutaneous skin incision was made over the middle of the medial thigh and the left saphenous nerve and artery were exposed and visualized with operating microscope. The cold collagen was injected around the saphenous nerve after gently coercing the needle through the neurovascular fascia with the needle bevel face up between the saphenous nerve and artery. The saphenous nerve should be over the bevel with the artery posterior to the needle tip. The collagen mixture was then extruded through the needle bevel until it was seen through an operating microscope to encircle the saphenous nerve in the neurovascular fascia. The entire 0.2 cc of collagen mixture may not need to be used. After collagen placement, visualization of the artery was done to ensure that a clear arterial pulse was present, without visible bleeding. The needle was withdrawn through the same hole in the fascia that was made on entry. The skin incision was closed with nylon sutures.

All rats were allowed to move freely within 20 minutes of surgery. There were no visible signs of edema, cyanosis, ecchymoses, or guarded gait after surgery, or at any later time. The ipsilateral plantar hind paws at the midfoot area were then tested biweekly for responses to light touch, pinprick, heat and cold as described above.

Example 2

Reversal of Mechanical Allodynia in a Mouse Model of Neurogenic Pain

Mice were prepared as described above by injecting collagen gel around the left posterior tibial nerve. All mice exhibited signs of neurogenic pain as determined by a mechanical allodynia response. After 79 days, six mice were selected for treatment with a mixture of a steroid (methyl-prednisolone 40 mg/ml) and 2% lidocaine as a way to reverse the neurogenic pain response. The mice were lightly anesthetized as before and 0.2 cc of a solution of 10% methyl-prednisolone and 90% lidocaine was injected by the left posterior tibial nerve via the posterior tibial tunnel as previously described; this was the same nerve where the collagen had been placed.

The animals were then again tested for a mechanical allodynia response as characterized by the number of paw withdrawals to light touch. The results were indicative of a reversal of the mechanical allodynia in four of the six mice tested. Two mice had continued pain responses to light touch up to day 118, with an average number of paw withdrawals of between 9 and 10. Four mice, however, had an average number of paw withdrawals at day 118 of 3.1, a value that was near the level of their own baseline averages (3.4) and that was significantly lower than was seen in these same animals before treatment (an average of 9.2). These data demonstrate that the mixture of steroid and lidocaine was able to reverse the signs of neurogenic pain in this animal model. Thus, based on the results of testing in this animal model, the mixture of a glucosteriod and/or an anesthetic would be a potential therapy for treatment of a nerve alteration or compression and associated pain.

Example 3

Guinea Pig Model for Neurogenic Pain

In order to extend the model to species other than rats and mice, four guinea pigs were subjected to the saphenous vein procedure as detailed above in rats using a purified Type II collagen material. Avitene, an absorbable, sterile, non-pyrogenic microfibrillar hemostat was the exact form of collagen used. Avitene (71 mg) was mixed with 0.5 cc normal saline to a viscous consistency. The mixture was then heated in a microwave for approximately 30 seconds at 80% power, in a porous ceramic bowl. This mixture was then injected near the saphenous nerve as described above in rats. After placement of the collagen colloid, the guinea pigs were observed and tested for their response to pinprick. All guinea pigs had a significant difference in pinprick tolerance after placement of the collagen as compared to their baseline measurements before collagen placement. The ipsilateral leg to the saphenous nerve procedure exhibited a lower weight pressure limit to pinprick, i.e., it was more sensitive to the pinprick, than the contra lateral leg when the animals were tested between days 24 to 35 post-surgery. This pinprick testing in the guinea pig demonstrated another pain behavior, known as mechanical hyperalgesia, or a lower tolerance to a normally painful stimulus.

What is claimed is:

1. A method for producing a non-human mammalian model for persistent neurogenic pain, comprising the step of: non-traumatically altering a tibial nerve or a branch of a tibial nerve of a non-human mammal by non-surgically placing a gel substance into the fascial tunnel through which the tibial nerve or the branch of the tibial nerve passes, wherein the placement of the gel substance leads to the development of allodynia, thereby producing a non-human mammalian model for persistent neurogenic pain.

2. The method of claim 1, wherein the gel substance comprises collagen.

3. A non-human mammalian model for persistent neurogenic pain, wherein a tibial nerve or a branch of a tibial nerve in the mammal has been non-traumatically altered by non-surgically placing a gel substance into the fascial tunnel through which the tibial nerve or the branch of the tibial nerve passes, wherein the placement of the gel substance leads to the development of allodynia.

4. The non-human mammalian model of claim 3, wherein the gel substance comprises collagen.

* * * * *